United States Patent [19]
Dashefsky

[11] Patent Number: 4,607,628
[45] Date of Patent: Aug. 26, 1986

[54] PATELLA SUPPORT BRACE

[76] Inventor: Joseph H. Dashefsky, 700 Old Country Rd., Plainview, N.Y. 11803

[21] Appl. No.: 737,249

[22] Filed: May 23, 1985

[51] Int. Cl.$^4$ ............................................. A61F 3/00
[52] U.S. Cl. ................................ 128/80 C; 128/80 F
[58] Field of Search ............... 128/87 R, 89 R, 80 C, 128/DIG. 15, 80 F, 88, 165; 2/22, 24

[56] References Cited

U.S. PATENT DOCUMENTS

| | | | |
|---|---|---|---|
| 1,601,659 | 9/1926 | Harlingen | 128/80 C |
| 2,587,166 | 2/1952 | Jovick | 128/80 C |
| 4,372,298 | 2/1983 | Lerman | 128/80 C |

FOREIGN PATENT DOCUMENTS 2724586 12/1978 Fed. Rep. of Germany .... 128/80 C
13630 of 1901 United Kingdom .............. 128/80 C

OTHER PUBLICATIONS

"New Method of Attaching Knee Cap", pp. 212–213, Francis S. Chambers.

Primary Examiner—Gene Mancene
Assistant Examiner—John G. Weiss
Attorney, Agent, or Firm—Mark T. Basseches; Paula T. Basseches

[57] ABSTRACT

A knee brace includes a patella support pad positioned to engage a lateral edge of the patella. The brace is adapted to apply a medially directed force to the patella pad responsive to movements of the leg from a flexed to an extended condition, the force being progressively relieved from the pad as the leg moves from the extended to the flexed condition.

7 Claims, 7 Drawing Figures

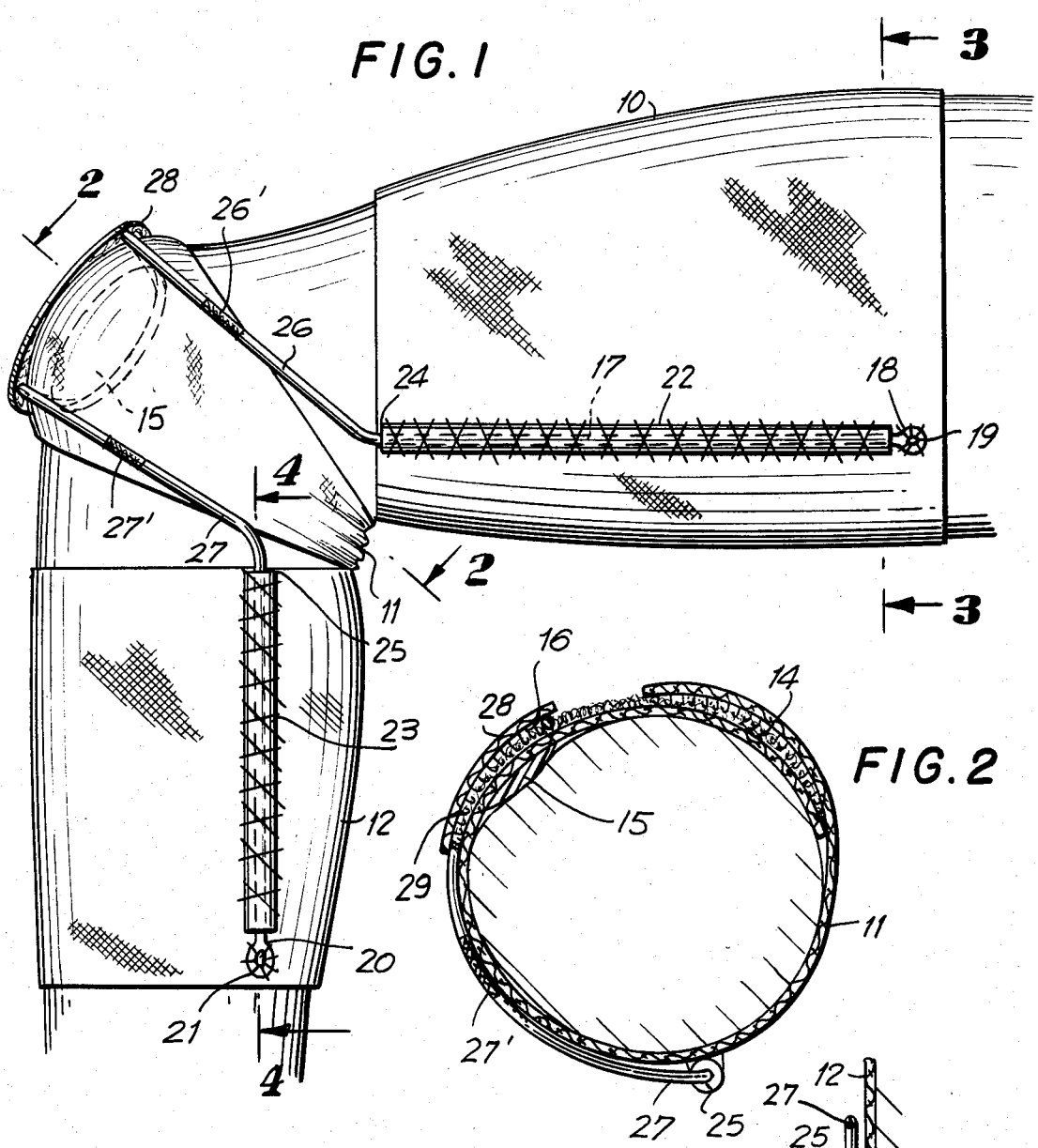
FIG.1
FIG.2
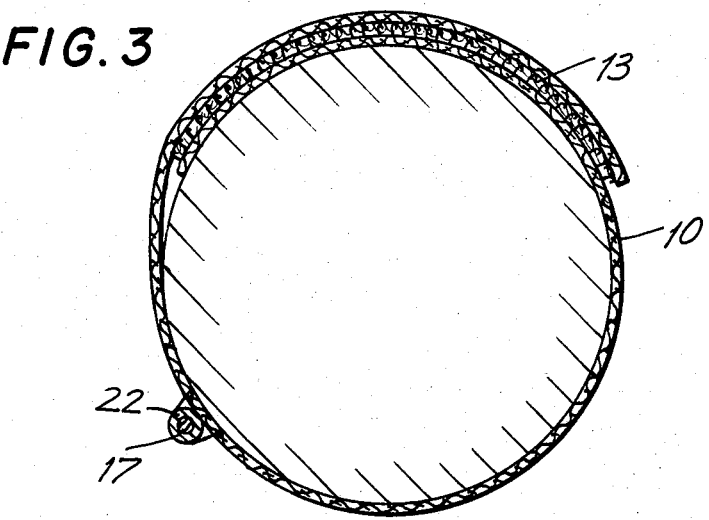
FIG.3
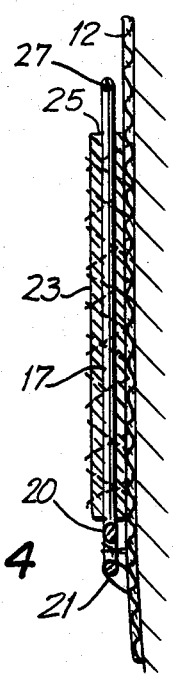
FIG.4

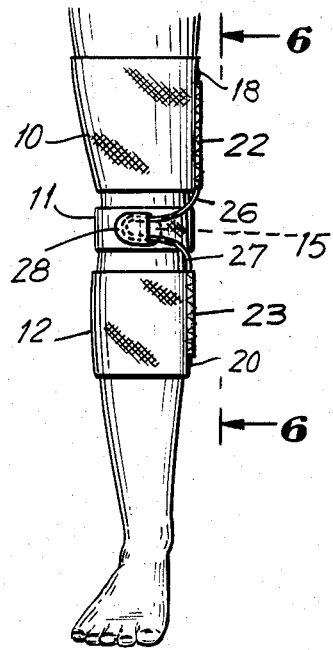
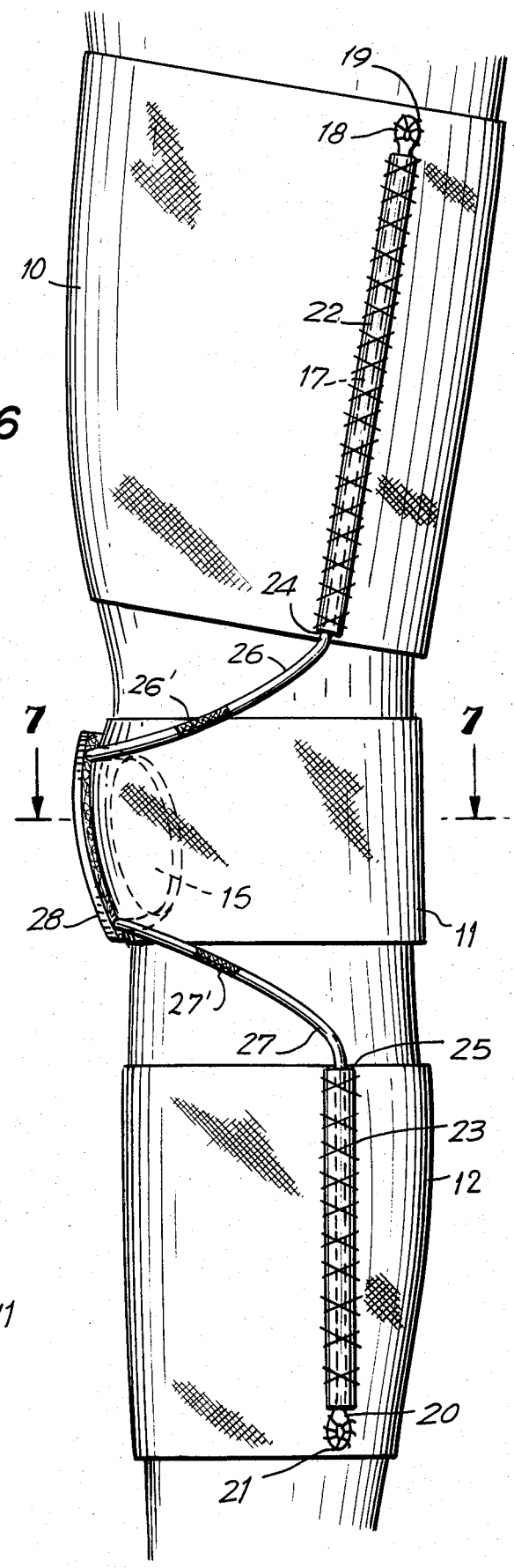
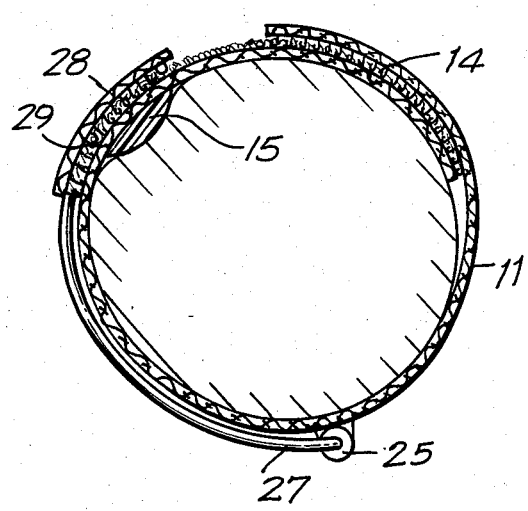

PATELLA SUPPORT BRACE

BACKGROUND OF THE INVENTION

1. Field of the Invention

The present invention relates to a knee brace and is directed more specifically to the provision of a patella support brace which is characterized in that a progressively increasing medially directed force is applied against the patella as the leg of the wearer shifts from a flexed to an extended condition.

2. The Prior Art

The patella of the knee joint rides in the femoral trochlea which is in the nature of a valley extending laterally of the joint. Secured to the patella and maintaining the same in its disposition within the trochlea is the upwardly directed patella ligament and downwardly directed tendons extending from the quadriceps muscles. The force angle of the quadriceps and patella tendons intersect and act on the patella at an obtuse and laterally outwardly directed angle known as the Q angle.

Due to the angular relationship of the forces exerted on the patella when the knee joint is shifted from the condition of flexion to a condition of extension, a laterally directed force vector, known as the valgus vector, is exerted against the patella. The valgus vector tends bodily to shift the patella outwardly progressively as the knee joint is straightened. Additionally, as the leg is straightened, a rotary movement is imparted to the lower leg components, functioning to increase the Q angle.

The femoral trochlea becomes progressively shallower in the area occupied by the patella as the knee joint approaches a condition of extension, and thus the constraining influence of the trochlea on the patella is progressively reduced as the leg approaches a fully extended condition.

The net effect of the various conditions above described, namely, valgus vector forces, rotation of the tibia during extension, and progressive depth reduction of the femoral trochlea, often lead, especially during violent activity, to a condition in which the patella subluxes or moves undesirably in a laterally outward direction relative to the femoral trochlea.

The subluxing forces exerted on the patella are often exacerbated by other stresses to which the knee joint is subjected in the course of physical activity.

Numerous attemps have been made to design knee braces which will prevent patella subluxation while at the same time avoiding discomfort to the wearer. No device hereotofore known has been entirely successful in accomplishing both of the noted results.

Numerous knee braces have been designed which include apertures intended to surround the patella and fix the patella against undue lateral outward movement. Alternative arrangements including cumbersome straps, bands and splints have been proposed, the objective in each instance being to confine the patella.

By way of example of braces appearing in the patent literature reference is made to the following patents: U.S. Pat. Nos. 1,388,772 of Aug. 23, 1921; 2,220,836 of Nov. 5, 1940; 2,270,685 of Jan. 20, 1942; 3,046,981 of July 31, 1962; 2,804,084 of Apr. 16, 1974; 3,945,046 of Mar. 23, 1976; 4,084,584 of Apr. 18, 1978; 4,116,236 of Sept. 26, 1978; French Patent No. 840,438 of Jan. 16, 1939, and British Patent No. 160,032 of 1898.

All of the above noted references represent examples of braces, sleeves or bands intended to minimize the likelihood of patella subluxation by the surrounding of or confinement of the patella, or restraint of the knee.

A slightly different approach to the problem is embodied in U.S. Pat. No. 4,296,744 of Oct. 27, 1981. In accordance with this patent, a patella pad is retained against the outer lateral surface of the patella. Elastic bands are secured to the patella pad in such manner that a resilient, medially directed force is exerted against the patella pad continuously throughout the range of movement of the knee joint.

The structure of the noted reference involves several major shortcomings. Specifically, since the force applied against the patella pad and, hence, against the patella, is continuously exerted, i.e. in condition of flexure where no restraining force is needed as well as at a condition of extension where it is required, the knee joint is subjected needlessly to a continuous compressive influence. Secondly, due to the geometry of the appliance, movement of the knee from the flexed to the extended condition actually reduces the force exerted against the patella progressively as the knee approaches a condition of extension Additionally, since the forces are continuously exerted, it is possible to apply relatively limited medially directed forces to avoid constriction and strangulation of the knee.

Thus the device acts in an exactly opposite way to an ideal condition wherein minimal forces are exerted when the knee is flexed, and the forces progressively increase as the knee approaches extension, the position at which the danger of subluxation is at its greatest.

Summary of the Invention

The present invention may be summarized as directed to a knee brace or patella splint wherein little or no medially directed forces are exerted against the patella when the knee is in flexed condition, the force progressively increasing as the leg approaches a condition of extension.

More particularly, the present invention is directed to a patella support device which relies on the straightening of the leg to produce kinetic forces of progressively increasing magnitude which are exerted against a patella pad increasingly to urge the patella pad in a medial direction against the lateral surface of the patella, thereby to reduce the possibility of subluxation of the patella.

Since the forces exerted against the patella during the initial ranges of movement, i.e. when the leg is in a fully flexed or a partially straightened condition, are low, there is little discomfort to the wearer as the patella is not forced bodily into the femoral trochlea. Where the leg approaches its condition of full extension, a very significant medial and/or combined medial and downward force is exerted against the patella.

It is accordingly an object of the invention to provide an improved knee splint or brace characterized in that a progressively increasing medial force is exerted on the patella responsive to movements of the leg to the flexed or straightened condition.

A further object of the invention is the provision of a device of the type described wherein the force noted is developed responsive to straightening of the leg whereby the force is automatically reduced when the leg is flexed and exerted at progressively increasing values as the leg approaches the extended condition.

To attain these objects and such further objects as may appear herein or be hereinafter pointed out, reference is made to the accompanying drawings, forming a part hereof, in which:

FIG. 1 is a side elevational view of a device in accordance with the invention applied to the leg of a wearer, the leg being in a condition of flexure;

FIG. 2 is a section taken on the line 2—2 of FIG. 1;

FIG. 3 is a section taken on the line 3—3 of FIG. 1;

FIG. 4 is a fragmentary vertical section taken on the line 4—4 of FIG. 1;

FIG. 5 is a front elevational view of the device, on a reduced scale, showing the leg in a condition of extension;

FIG. 6 is a magnified side elevational view of the device taken in the direction of the arrows 6—6 of FIG. 5;

FIG. 7 is a horizontal section taken on the line 7—7 of FIG. 6.

Referring now to the drawings, the device of the present invention is comprised generally of three cuffs or bands 10, 11, 12 encircling, respectively portions of the thigh, knee joint and calf of the wearer. While the elements 10, 11, 12 have been illustrated and described as three discrete units, it will be readily appreciated that the same may consist of a single elongate band or cuff with appropriate cutouts between the respective parts.

The bands 10 and 12 may be formed of unitary annular configuration snugly to fit the thigh and calf portions of the wearer, the bands being of elastic material so as to retain their position on the limb. Optionally, as shown in FIG. 3 for example, the cuff 10 may be comprised of a band including overlapping Velcro (trademark) or like attachment means 13 to enable the cuff to be accommodated to a range of sizes of individuals.

The cuff 12 may, in similar fashion, be rendered adjustable in circumference.

The central cuff 11 is also preferably circumferentially adjustable as by the inclusion of complemental Velcro components in the area 14.

The cuff 11 includes a patella pad 15 which is adapted to be positioned laterally outwardly of the crest of the patella, the pad desirably including a component at least partially encircling or bearing against portions of the upper crest of the patella.

The outer upper surface of the band 11 in registry with the pad 15 includes a circumferentially extending length of Velcro components in the area 16.

It will be appreciated from the ensuing description that the Velcro components in the area 16 are intended adjustably to receive complemental Velcro components of a force developing means which will exert a medially directed force on the pad responsive to straightening of the leg.

More specifically and by way of example but without limitation, a form of force developing means is comprised of a flexible elongate cable member 17 having a first end 18 secured to a gusset or reinforcement 19 on the thigh encircling cuff 10. The opposite end 20 of the cable 17 is secured to gusset 21 adjacent the lower end of the calf encircling cuff 12.

It is to be noted that the points of attachment of the ends 18 and 20 lie rearwardly or posteriorly of the axis of rotation of the knee joint.

The cable 17 is slidably received within an upper sheath portion 22 fixed to the thigh cuff 10. Similarly a sheath 23 fixed to the calf cuff 12 slidably contains portions of the cable running adjacent the calf.

The cable 17 emerges from sheaths 22 and 23 at reinforced exit portions 24, 25, respectively, which exit portions are preferably fitted with wear-resistant eyelets (not shown).

The portion of the cable between the exit portions 24, 25 defines a bight portion which includes the legs 26, 27. The distal ends of the legs 26, 27 are secured to a web 28, the inner or underface of which is provided with complemental Velcro fastening material 29 adapted to grip to the Velcro components 16. Optionally, the legs 26, 27 of the bight may include interposed elastic lengths 26', 27' which function as a force adjustment medium.

The operation of the device will be apparent from the preceding description.

The cuffs 10, 11, 12 are applied in the manner shown, the cuff 11 being applied in such manner that the patella pad 15 encompasses the outer lateral crest and preferably portions of the upper crest of the patella.

With the cuffs thus applied and with the leg in a flexed condition, as shown in FIG. 1, the web 28 secured to the bight legs 26, 27 is drawn outwardly to a condition of slight tension, at which position it is pressed against the Velcro components 16 above the patella pad.

As will be appreciated, where the bight components include elastic elements 26', 27', the web may be applied with a slight prestressing of the cable.

When the wearer extends his leg to the position shown, for example in FIG. 7, the distance between the ends 18 and 20 of cable 17 will increase due to their connection posteriorly of the pivot axis of the knee joint. In the course of such straightening action increments of the cable 17 will be drawn into the sheaths 22, 23, with resultant shortening of the bight portions 26, 27 and a consequent pulling of the web 28 in a medial direction whereby, due to the connection of the web and patella pad assembly, the patella pad will be shifted in a medial direction.

As will be understood from the foregoing description, the apparatus will exert little or no medial force on the patella pad when the leg is in a condition of flexion, depending of course on the tension imparted to the cable when the web 28 is secured to the patella pad assembly. As the leg straightens, however, a progressively increasing force is exerted against the patella pad and, accordingly, the patella.

It is important to note that the present apparatus is readily distinguishable from any patella brace heretofore knoWn in that the force exerted against the patella in a medial direction is developed responsive to the straightening of the leg. Heretofore the patella restraints have resulted from attempts to constrain the patella or apply essentially constant elastic forces against the patella.

With the device of the present invention, the patella is essentially unconstrained when the knee is fully bent, yet significant forces of several pounds or more may be developed against the patella by the movement of the leg to the straightened or extended condition.

As will be evident to those skilled in the art, numerous variations in details of construction may be made without departing from the spirit of the present invention which is considered to be directed broadly to the concept of utilizing the straightening action of the leg to create medial forces acting against the patella.

By way of example, the specific means or mechanism for developing the medial force exerted on the patella pad responsive to straightening of the leg need not be comprised of the cable arrangement illustrated. For instance, the brace may be provided with splints having interengaging cam surfaces which deflect, via a pulling or pushing mechanism, the patella pad in an inward direction responsive to articulation of the leg from the flexed to the straightened condition.

As a further alternative, the medial force on the patella pad may be developed by a cable wrap arrangement whereby a cable attachable to the patella pad is wrapped about an arcuate surface and, hence, foreshortened responsive to movements of the leg from the flexed to the extended condition.

Accordingly the invention is to be broadly construed within the scope of the appended claims.

Having thus described the invention and illustrated its use, what is claimed as new and is desired to be secured by Letters Patent is:

1. A knee brace adapted to support the patella of a wearer comprising a patella pad, means for maintaining said pad laterally adjacent the patella of a wearer, and laterally shiftable force developing means operatively connected to said pad for urging said pad laterally in a medial direction thereby to exert progressively increasing, medially directed forces upon said pad responsive to articulating movements of the leg from a flexed to an extended condition.

2. A brace in accordance with claim 1 wherein said force developing means comprises means for shifting said pad in a medial direction responsive to said articulating movements of the leg.

3. A brace in accordance with claim 1 wherein said developing means comprises an elongate tension member having a first end portion secured to the leg of a wearer above the knee and posteriorly located with respect to the pivot axis of the knee, a second end portion secured to the leg at a position below the knee at a position posteriorly located with respect to the pivot axis of the knee, and a central, laterally outwardly directed bight portion, the combination including attachment means for connecting said bight portion to said patella pad.

4. A brace in accordance with claim 3 wherein said attachment means is adjustably connectible to said pad.

5. A brace in accordance with claim 4 wherein said tension member includes elastically extendible portions.

6. A brace in accordance with claim 5 wherein said elastically extensible portions are disposed in the area between said bight portion and said adjustable attachment means.

7. A brace in accordance with claim 6 wherein said adjustable attachment means comprises complemental Velcro components on said patella pad and said bight portion.

* * * * *